United States Patent
Patten et al.

(10) Patent No.: US 6,612,186 B1
(45) Date of Patent: Sep. 2, 2003

(54) MASS FRACTION METERING DEVICE

(75) Inventors: Andrew T. Patten, Boulder, CO (US); Thomas A. O'Banion, Longmont, CO (US); Julie Ann Valentine, Reno, NV (US)

(73) Assignee: Micro Motion, Inc., Boulder, CO (US)

( * ) Notice: Subject to any disclaimer, the term of this patent is extended or adjusted under 35 U.S.C. 154(b) by 0 days.

(21) Appl. No.: 09/505,276

(22) Filed: Feb. 16, 2000

(51) Int. Cl.$^7$ .................................................. G01F 1/74
(52) U.S. Cl. ........................................ 73/861.04; 73/861
(58) Field of Search ............................ 73/861, 861.04, 73/861.03, 861.02, 23.2, 31, 61.44

(56) References Cited

U.S. PATENT DOCUMENTS

| | | |
|---|---|---|
| 5,323,657 A | 6/1994 | Vander Heyden |
| 5,604,316 A * | 2/1997 | Alonso ..................... 73/861.04 |
| RE35,639 E * | 10/1997 | Vander Heyden et al. .......... 73/863.03 |
| 5,807,749 A | 9/1998 | Hornemann |
| 5,873,351 A * | 2/1999 | Vars et al. ..................... 73/202 |
| 5,913,239 A * | 6/1999 | Morris, Jr. et al. ......... 73/118.2 |
| 5,944,048 A * | 8/1999 | Bump et al. ............. 137/487.5 |
| 5,975,126 A * | 11/1999 | Bump et al. ............. 137/487.5 |
| 6,053,054 A * | 4/2000 | Wusterbarth et al. .... 73/861.28 |
| 6,094,940 A * | 8/2000 | Fujiwava et al. ............ 65/17.4 |

FOREIGN PATENT DOCUMENTS

EP      0 543 273 A2      5/1993

* cited by examiner

*Primary Examiner*—Hezron Williams
*Assistant Examiner*—Andre Allen
(74) *Attorney, Agent, or Firm*—Duft, Setter, Ollila & Bornsen LLC

(57) ABSTRACT

An energy metering device includes a volumetric flow meter or mass flow meter in combination with a gas analyzer that provides telemetry regarding the constituents of a natural gas flow stream. An interpreter analyzes this information and provides a real time output corresponding to the enthalpy of combustion for the gas stream. This output is used to adjust or throttle the gas flow stream for purposes of delivering the flow stream according to a preselected parameter, which is related to desired operating conditions for a combustion device including a boiler or an engine.

25 Claims, 1 Drawing Sheet

MASS FRACTION METERING DEVICE

BACKGROUND OF THE INVENTION

1. Field of the Invention

The present invention pertains to the field of mass flow metering devices, such as Coriolis flow meters. More specifically, the metering devices are used in combination with other devices or estimation techniques that determine the composition of fluid in a flow stream by mass fraction on a real-time basis to gain superior measurement accuracy.

2. Statement of the Problem

Industrial processes that consume or transport petrochemical liquids and gasses often use a mixture of compounds, e.g., methane, ethane, propane, and butane in a single mixture. It is often important to know the percentage of the total mixture that consists of a single type of compound. In this context, representation of the compound in the mixture is often discussed in terms of a mole fraction or a mass fraction. The term "mass fraction" means a percentage of a mixture allocated to a single compound or group of compounds on a mass basis. Similarly, the term "mole fraction" means a percentage of a mixture allocated to a single compound or group of compounds on a mole basis. It has been a conventional practice to calculate mole or mass fractions based upon volumetric measurements of the combined flow stream that are converted to mass using various empirical correlations or density measurements. This conversion process adds uncertainty and error into the mass fraction determination.

A specific example where it is desirable to ascertain mass fractions or mole fractions from a flow stream exists in the petrochemical refining industry. Engineers are constantly reviewing process efficiencies in the cracking of various feedstocks to convert these feedstocks into refined products, e.g., as in the flame-cracking process of making ethylene directly from petroleum by combustion at 2000° F. using a mixture of napthalene or crude oil and high temperature gasses with support from pure oxygen. Depending upon the nature of the crude oil and the availability of gasses, the reaction temperature and timing may be adjusted to optimize the economic recovery from use of the reactor vessel. Mass balance calculations based upon compositional fractions in the flow stream are often essential to these general types of calculations. In this context of process fine-tuning adjustments, it is not only useful to know the percentage composition of the incoming fuel stream, but it is also useful to know the percentage composition of the reaction products. These measurements are typically performed on volumetric percentages, as opposed to mass percentages.

Another specific instance where it is desirable to know the fractional breakdown of a flow stream exists in the use of pipelines for transportation and delivery of natural gas and other fuels. Fuels are typically sold on a volumetric basis, but the heating value may vary by more than fifty percent on a constant volumetric basis depending upon variation of the fuel composition over time.

Yet another example of a need for mass fraction analysis exists in instances where neither mass nor volume are measured. For example, an internal combustion engine or an industrial boiler may be operated for the express purpose of burning fuels to produce electricity. The engine is used to turn a small generator for this purpose. The boiler may be used to make steam that drives a larger generator. While the ultimate goal is to harness energy from these fuels, the energy throughput into the engine is not measured.

It is substantially impossible to perform a direct or indirect measurement of chemically available energy that resides in a feedstock based upon an analysis of work output and system energy losses. The act of combustion is associated with an efficiency loss, e.g., 40% to 60%, in which a portion of the chemically available energy stored in the feedstock is lost to entropy because it cannot be converted into useful work. For example, heat is lost by convection and radiative transfer. Exhaust gasses are hotter due to the exothermic nature of combustion. Fuels almost never have consistent quality. These factors combine to prevent the monitoring of combustion efficiency as an indicator of efficiency or impending mechanical failure in a mechanical device.

Boilers and engines may be adapted to use different fuels. For example, a dual-purpose boiler may be easily converted from use with a gas feedstock to use with a liquid feedstock. This type of switching boiler has application in the public service company sector where an electric company may wish to switch between fuels to minimize its expenditures for fuel or to reduce levels of regulated emissions. It can be very difficult to switch a boiler from oil to gas and then to ascertain how much gas must be consumed to replace the oil when the nature and content of the gas fuel is unknown.

Even where the change in feedstock is not so drastic as a switch from oil to natural gas, the feedstocks themselves vary in quality and composition over time. Diluents including carbon dioxide, nitrogen, water, and hydrogen sulfide are commonly found in natural gas flow streams. Furthermore, the relative percentages of constituents in natural gas have large variations by producing region, in addition to variations from well to well in a selected producing region. Thus, gas that is produced from the Gulf of Mexico region may have a lower specific gravity and energy content than gas that is produced in Nigeria or California. Similarly, the nature of crude oil varies from tar-like substances to thinner oils that pour easily and have a light brown color. In transportation, individual flow streams are mixed and combined as the materials are transported by pipeline or by ship from the producing regions to the consuming regions. Each flow stream has its own composition and specific heating value.

An engine or boiler operates at a different efficiency depending upon the nature and quality of the fuel that it burns. Even where an engine rotates at a constant speed, a change in feedstock constituents by the addition of diluents may make less torque available from the engine. Similarly, a boiler may make less steam. The combustion devices may suffer a diminution in or improvement in efficiency if a natural gas supply changes to one having relatively more methane. If only the heating content of the fuel were known, it would be possible to alter the operating conditions of a combustion device according to a preselected parameter, such as a change in volumetric or mass flow rate to provide a constant energy source or operation of the device within a preferred range for obtaining an optimal fuel efficiency.

As reported in Snell et al., Installation of Multipath Ultrasonic Meters on a Major Australian Metering System Project, in December of 1996, multipath ultrasonic flow meters (volumetric meters) were installed on an Australian natural gas pipeline for use as custody transfer meters at all offtakes from the transmission system into local distribution systems. The meters were each coupled with a gas chromatograph that analyzed the flow stream constituents. The mass flow measurements were converted to volume and volume-based enthalpy values were calculated for the flow stream. Ultrasonic meters were chosen for the study because they were reported to have the least uncertainty in measurement for both volume and energy content for the flow rates in the study. Coriolis meters were listed as possible alternatives to obtain volumetric flow measurements using AGA equations to convert the mass flow readings into volume, but Coriolis meters were also characterized as having the greatest uncertainty in energy measurements, i.e., 3.0% versus 1.0% for ultrasonic meters. All of the energy uncertainties for all types of meters in the study were presented as being greater than the volume uncertainties.

As shown in the above discussion, a mass-based metering device that could provide an accurate real time determination of the mass fractions in a flow stream would facilitate mass balance calculations in petrochemical refining, as well as open new horizons in the ability to conserve and sell energy values with decreased levels.

SUMMARY OF INVENTION

The present invention overcomes the problems outlined above by providing a metering device that affords extremely accurate direct measurements concerning the mass fractions of a flow stream. These mass fractions may then be related to mass balance calculations in petrochemical refineries, as well as heat content or other enthalpy-related values that are available from a flow stream. Accuracy is improved by avoiding the former necessity of converting mass based flow measurements to volumetric measurements as a condition precedent to ascertaining mass fractions.

The metering device is used to provide real time telemetry concerning mass fractions in a flow stream having multiple constituents. A Coriolis mass flow meter or other mass-based flow meter is used to measure a mass flow rate in the flow stream and to provide first signals representative of the mass flow rate. A chromatograph, density or pressure measurement combined with an empirical correlation, or other means for analyzing the content of the flow stream is used to determine constituent percentages of the flow stream and to provide second signals representative of the constituent percentages.

In preferred embodiments, a central processor, computer or controller is used to interpret the first signals and the second signals received from the analyzing means to provide output representing an energy value in the flow stream. The energy value derived by multiplication of the mass flow rate times the constituent percentages times mass-based energy values of constituents corresponding to the constituent percentages. This computational technique is advantageous because it permits a direct or mass-based computation of energy content in the flow stream while minimizing intermediate correlations, such as correlations approximating the nonideal behavior of real gasses.

In still other preferred embodiments, the energy metering device is operably coupled with a throttle to control flow based upon energy content of the flow stream based upon a preselected parameter. According to principles of the invention, the preselected parameter may include delivery of a substantially constant rate of energy for release by combustion, delivery of energy at a rate within a preferred operating range for a combustion device, or delivery of time-controlled sales of energy content in the flow stream.

When the mass flow meter is a Coriolis meter, the meter can also be operated as a densitometer, and the density readings can be used to associate the flow stream with an empirical correlation of energy content, as an alternative to use of a chromatograph to analyze constituent percentages.

These objects and advantages of the invention, as well as other features of the invention, will be apparent to those skilled in the art upon reading the following description together with the associated drawings. It is an aspect of the invention to provide the mass fraction flow readings by direct measurement, as opposed to empirical correlations. It is a further aspect of the invention to provide greater accuracy in energy content measurements by applying mass based correlations when empirical correlations are utilized. Yet another aspect of the invention is to apply these improved measurements in automated processes, such as the calculation of energy values based upon fractionated mass flow together with the throttling of an internal combustion engine based upon fuel energy consumption.

DETAILED DESCRIPTION OF THE PREFERRED EMBODIMENTS

The Energy Measurement Device

Figure 1:
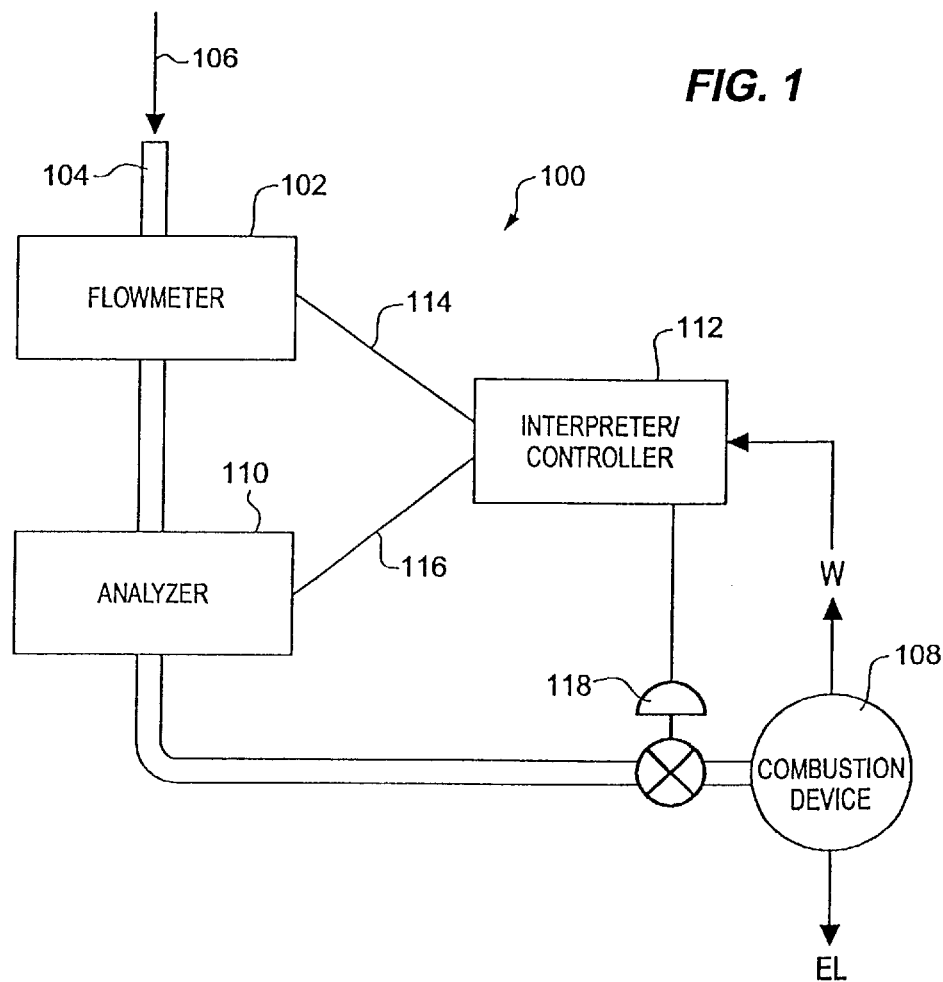
FIG. 1 is a schematic diagram of an energy metering device according to the present invention.

FIG. 1 depicts a schematic diagram of an energy measuring device 100 according to the present invention. A flowmeter 102 is operably connected to a flow line 104 for purposes of measuring a flow rate in a flow stream 106 of fuel for ultimate use in combustion device 108, e.g., a boiler or an engine. A flow stream analyzer 110 is similarly coupled with flow line 104 for the purpose of analyzing the composition and nature of flow stream 106. Analyzer 110 measures intrinsic properties of the flow stream, such as density or specific gravity, or percentages of the flow stream that are allocated to different chemical compositions, e.g., methane, ethane, butane, propane, pentane, hexane, heptane, octane, nonane, and decane, alternatively, analyzer 110 represents a computer memory or algorithm that estimates a constant energy content of the flow stream on a per unit mass basis. Flowmeter 102 and analyzer 110 perform their respective direct measurements and send signals representative of these measurements to interpreter/controller 112 on lines 114 and 116. The interpreter/controller 112 applies a mathematical algorithm using information from these signals as input to provide an output representing the amount of enthalpy or the heating value that is available from combustion of the fuel in flow stream 106. Based upon the output, interpreter/controller 112 adjusts a remotely actuatable valve 118 to act as a throttle in providing fuel to the combustion device 108 based upon a preselected parameter governing the operation of combustion device 108. In turn, the combustion device produces a work output W and an efficiency loss EL.

The flowmeter 102 can be any mass flowmeter, preferably including a Coriolis mass flow meter. The analyzer can be a gas chromatograph, a densitometer, conductivity meter, or any other device for measuring intrinsic fluid properties that can be related to the energy content of the fluid. Where the flowmeter 102 is a Coriolis flow meter, it is possible to operate the flowmeter as a vibrating tube densitometer or as a capillary tube viscosimeter by conventional practices according to the manufacturer's specifications. Either of these intrinsic fluid properties may be correlated to the energy content of the fuel on a per unit mass basis. Thus, the separate boxes shown in FIG. 1 as flowmeter 102 and analyzer 110 would merge into a single Coriolis flowmeter having different operational modes. Similarly, the interpreter/analyzer 112 may consist of an integrated CPU and controller or the CPU and controller may be separate devices.

Manner of Operation

Figure 2:
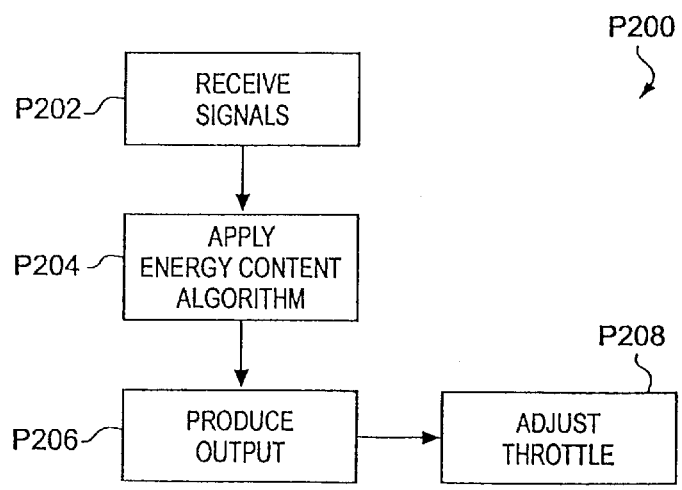
FIG. 2 is a process control flow chart demonstrating operation of an signal interpreter that determines an amount of energy flowing through the energy metering device shown in FIG. 1.

FIG. 2 depicts a schematic process diagram showing operation of the interpreter/controller 112. The interpreter/controller 112 receives a first signal from flowmeter 102 (see FIG. 1) representing a volumetric or mass flow rate of flow stream 106. Interpreter/controller 112 receives a second signal from the analyzer 104 representing intrinsic properties or constituents of the flow stream 106. In this discussion, the terms "first signal" and "second signal" do not necessarily convey a sequence of events in time, rather, the terms are merely used to distinguish the signals. The signals may be transmitted to interpreter/controller in any order including simultaneous transmission.

In step P204, interpreter/controller 112 applies an algorithm, statistical technique or data mapping technique to assign a heating value to the flow stream. This heating value is any enthalpy-related measure of energy content in the fuel that may be released by combustion. Representative values for energy content include terms that are known in the art as gross heating value (wet or dry), net heating value, enthalpy of combustion, and specific heat. An output from step P204 appears in step P206, and step P208 includes interpreter/controller adjusting valve 118 to govern the operation of combustion device 108 according to a preselected parameter. Suitable parameters for governing the operation of combustion device 108 include, among others:

1.) application of fuel energy at a constant rate for consumption at a constant energy rate in combustion device 108;
2.) application of fuel energy at rate producing a constant work output W from combustion device 108 corrected for variations in operating efficiency due to fuel energy content; and
3.) sale of fuel based upon energy content of the fuel for eventual use in combustion devices of the type shown as combustion device 108.

The Energy Content Algorithm

There are many ways to calculate or estimate the energy content in a flow stream. Perhaps the simplest way is to make an educated guess as to the per unit mass energy content, as confirmed by laboratory tests or measurements performed on samples of fuel in the flow stream. Another way is to obtain multiple types of input data for use in training a conventional data mapping technique, such as an adaptive filter or neural network. These multiple types of input data could include viscosity, density, temperature, and pressure, all of which may be obtained from conventional Coriolis flowmeters together with conventional transmitters, e.g., temperature and pressure transmitters, that are used in Coriolis measuring devices. In yet another alternative, many different types of algorithms are known for their ability to relate energy content to fuel based upon intrinsic properties of the fuel. For example, a calorimeter may be used to burn a fuel and the heat content may be correlated to density, viscosity or gravity of the fuel.

The fuel of choice for many industrial uses is natural gas. In this case, there are many excellent algorithms available that can be used to calculate the precise heating value of the gas flow stream based upon published information concerning the constituents of the gas. Table 1 below provides exemplary published information for substantially all constituents that will comprise an appreciable percentage of any natural gas. It is significant that the enthalpy of combustion for hydrocarbons expressed as kJ/g for each flow component is almost a constant value that varies by 7 to 15% of the methane energy content and varies by lesser percentages for among propane and higher hydrocarbons.

TABLE 1
PROPERTIES OF NATURAL GAS CONSTITUENTS

| Constituent | Gas Gravity* | Net Heating Value (Btu/SCF) | Enthalpy of Combustion $-\Delta_c H_f$ (kJ/mole) | Molecular Weight (g/mole) | Enthalpy of Combustion (kJ/g) |
|---|---|---|---|---|---|
| $N_2$** | 0.9672 | 0 | 0 | 28.01 | 0.00 |
| $CO_2$ | 1.5195 | 0 | 0 | 44.00 | 0.00 |
| $H_2S$ | 1.1765 | 588 | 672.4 | 34.08 | 19.73 |
| Methane | 0.5539 | 909.1 | 889.7 | 16.04 | 55.47 |
| Ethane | 1.0382 | 1617.8 | 1559.1 | 30.07 | 51.85 |
| Propane | 1.5225 | 2316.1 | 2217.0 | 44.10 | 50.27 |
| Isobutane | 2.0068 | 3001.1 | 2866.3 | 58.12 | 49.32 |
| N-butane | 2.0068 | 3010.4 | 2874.9 | 58.12 | 49.46 |
| Isopentane | 2.4911 | 3698.3 | 3525.6 | 72.15 | 48.86 |
| N-pentane | 2.4911 | 3707.5 | 3532.4 | 72.15 | 48.96 |
| N-hexane | 2.9753 | 4403.7 | 4191.1 | 86.18 | 48.63 |
| N-heptane | 3.4596 | 5100.2 | 4849.3 | 100.20 | 48.40 |
| N-octane | 3.9439 | 5796.7 | 5507.2 | 114.23 | 48.21 |
| N-nonane | 4.4282 | 6493.3 | 6166.4 | 128.26 | 48.08 |
| N-decane | 4.9125 | 7188.6 | 6823.9 | 142.28 | 47.96 |
| $O_2$ | 1.1048 | 0 | 0 | 32.00 | 0.00 |
| $H_2$ | 0.0696 | 274 | 285.6 | 2.02 | 141.39 |
| He | 0.138 | 0 | 0 | 4.00 | 0.00 |
| $H_2O$ | 0.622 | 0 | 0 | 18.02 | 0.00 |

*Relative to air where air = 1.

Where the flow rate measurements are performed on a mass per unit time basis, it is a simple matter to calculate the mass fractions in a flow stream according to principles of the invention. The mass fractions are calculated according to Equation (1):

$$Q_C = \Sigma_i^n X_{mi} Q_m \quad (1)$$

where n represents the total number of thermodynamically significant flow components in the total flow stream, i denotes a property for an individual flow component, $Q_C$ is a mass content of a total flow stream allocated to a flow component comprising part of a total flow stream, fraction, $X_{mi}$ is a mass fraction of the total flow stream allocated to the flow component as determined by a chromatograph or other instrument for this purpose, and $Q_m$ is the total mass flow rate.

The total energy content can be calculated based upon Equations (1) and (2)

$$Q_E = \Sigma_i^n Q_C H_{fi} \quad (2)$$

where $Q_E$ is the total energy flow rate in energy per unit time, n represents the total number of thermodynamically significant flow components in the total flow stream, i denotes a property for an individual flow component, $Q_C$ is defined above, and $H_{fi}$ is the enthalpy of combustion for a particular constituent denoted as energy per unit mass. The $H_{fi}$ enthalpy value is understood to mean the energy released by a complete combustion where the reaction products are gaseous water and $CO_2$, but other forms of heating value measurement may be substituted for $H_{fi}$ including net heating value, gross heating value wet and gross heating value dry, or any other commonly understood measurement of heating value.

Where a gas chromatograph or other mechanism for analyzing the hydrocarbon fractions in the organic flow stream is unavailable, such as when the instrument breaks down or costs too much for a specific application, the energy content may be estimated by assuming an average constant energy value per unit mass, e.g., as in the kJ/g column of Table 1. Where the flow stream is a gas flow stream, the flow stream usually comprises 60% to 90% methane, and a good average value is in the range of 52 to 53 kJ/kg. A value of 48 kJ/kg may be assumed for liquid flow streams. These estimates are typically accurate to within three to five percent, assuming that the flow stream is not contaminated with excessive amounts of diluents, e.g. carbon dioxide, water, or hydrogen sulfide.

Volumetric gas measurements must refer to a base or reference pressure and temperature, which are usually referred to in the art as standard conditions, i.e., 60° F. and 14.7 psia. Thus, $$Q_E = \Sigma_i^n X_{vi} Q_{v\ std} H_{v\ std i} \quad (3)$$

where $Q_{v\ std}$ is a volumetric flow rate of the entire gas flow stream corrected to standard conditions, $H_{v\ std i}$ is the enthalpy of combustion for a particular constituent denoted as energy per unit volume at standard conditions, $X_{vi}$ is a mole fraction of the total gas flow stream allocated to an individual constituent, and the remaining terms are defined above. Also, for each constituent according to Equation (4), $$H_{v\ std i} = (H_{fi}) \times (\rho_{std}) = \left(\frac{H_{molei}}{MWi}\right) \times \left(\frac{144\ MWiP}{1545\ TZ}\right) \quad (4)$$

where $H_{molei}$ is enthalpy of combustion as energy per mole as shown in Table 1 above, MWi is molecular weight as shown in Table 1 above, $\tilde{n}_{std}$ is the gas density at standard pressure, P is absolute pressure in the flow system in psia, T is temperature in the flow system in degrees Kelvin, Z is the ideal gas deviation factor at internal flow system temperature and pressure, and the remaining terms are defined above.

The problem that arises with volumetric conversions of this nature is that empirical correlations introduce error into the calculation. Specifically, the gas deviation factor Z may be inaccurate to an extent that exceeds the meter uncertainty. This source of error is avoided by methods and apparatus of present invention.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

We claim:

1. A metering device for use in providing real time telemetry concerning a flow stream having multiple constituents, said metering device comprising:
   a mass flow meter operable to measure a mass flow rate in said flow stream and to provide signals representative of said mass flow rate;
   means for calculating a mass-based combustion energy content of said flow stream based upon said signals representative of said mass flow rate; and
   means for providing output representative of said mass-based combustion energy content of said flow stream.

2. The metering device as set forth in claim 1 wherein said means for calculating a mass-based combustion energy content includes means for analyzing said flow stream, when said flow stream is directed through said mass flow meter, to determine constituent percentages of said flow stream and for providing signals representative of said constituent percentages.

3. The metering device as set forth in claim 2 wherein said means for calculating a mass-based combustion energy content includes means for interpreting said signals representative of said mass flow rate and said signals representative of said constituent percentages to provide output representing an energy value for said flow stream flowing through said mass flow meter, said energy value derived by the multiplication of said mass flow rate times said constituent percentages times mass-based energy values of constituents corresponding to said constituent percentages.

4. The metering device as set forth in claim 1 wherein said means for calculating a mass-based combustion energy content includes means for multiplying a mass corresponding to said signals representative of said mass flow rate by a constant assumed energy content per unit mass.

5. The metering device as set forth in claim 1 including a throttle to control flow of said flow stream responsive to variances in a preselected parameter.

6. The metering device as set forth in claim 1 wherein said mass flow meter comprises a Coriolis meter.

7. The metering device as set forth in claim 2 wherein said means for analyzing includes means for operating a Coriolis meter as a densitometer to obtain a representative density reading from said flow stream.

8. The metering device as set forth in claim 7 wherein said means for analyzing comprises a densitometer.

9. The metering device as set forth in claim 8 wherein said means for calculating a mass-based combustion energy content includes means for associating said density of said flow stream with an enthalpy related value based upon information obtained from said densitometer.

10. The metering device as set forth in claim 2 wherein said means for analyzing comprises a chromatograph.

11. The metering device as set forth in claim 10 wherein said means for calculating includes means for calculating an enthalpy related value based upon information obtained from said chromatograph.

12. The metering device as set forth in claim 5 wherein said preselected parameter comprises delivery of a substantially constant rate of energy for release by combustion.

13. The metering device as set forth in claim 5 wherein said preselected parameter comprises delivery of energy at a rate within a preferred operating range for a combustion device.

14. The metering device as set forth in claim 5 wherein said preselected parameter comprises delivery of time-controlled sales of energy content in said flow stream.

15. A method for providing real time telemetry concerning a flow stream having multiple constituents, said method comprising the steps of:
   measuring a mass flow rate in said flow stream;
   providing signals representative of said mass flow rate;
   calculating a mass-based combustion energy content of said flow stream based upon said signals representative of said mass flow rate; and
   providing output representative of said mass-based combustion energy content.

16. The method according to claim 15 wherein said step of calculating a mass-based combustion energy content includes:
   analyzing said flow stream to determine constituent percentages of said flow stream and providing signals representative of said constituent percentages of said flow stream; and
   interpreting said signals representative of said mass flow rate and said signals representative of said constituent percentages to provide output representing an energy value in said flow stream, said energy value being derived by the multiplication of said mass flow rate times said constituent percentages times mass-based energy values of constituents corresponding to said constituent percentages.

17. The method according to claim 15 wherein said step of measuring a mass flow rate comprises measuring a mass flow rate through use of a Coriolis meter.

18. The method according to claim 17 including a step of operating said Coriolis meter as a densitometer to obtain a representative density reading from said flow stream.

19. The method according to claim 18 wherein calculating a mass-based combustion energy content includes associating said density of said flow stream with an enthalpy related value based upon information obtained from said densitometer.

20. The method according to claim 16 wherein said step of analyzing said flow stream is performed using a chromatograph.

21. The method according to claim 20 wherein said step of interpreting includes calculating an enthalpy related value based upon information obtained from said chromatograph.

22. The method according to claim 15 including a step of throttling said flow stream to control flow responsive to variances in a preselected parameter.

23. The method according to claim 22 wherein said preselected parameter comprises delivery of a substantially constant rate of energy for release by combustion.

24. The method according to claim 22 wherein said preselected parameter comprises delivery of energy at a rate within a preferred operating range for a combustion device.

25. The method according to claim 22 wherein said preselected parameter comprises delivery of time-controlled sales of energy content in said flow stream.

* * * * *